United States Patent
Zeng et al.

(12) 
(10) Patent No.: US 12,153,058 B2
(45) Date of Patent: Nov. 26, 2024

(54) TEST KIT FOR TESTING FAT-SOLUBLE VITAMINS IN SERUM USING HIGH PERFORMANCE LIQUID CHROMATOGRAPHY COUPLED WITH TANDEM MASS SPECTROMETRY

(71) Applicant: Hangzhou Calibra Diagnostics Co., Ltd., Hangzhou (CN)

(72) Inventors: Shanshan Zeng, Hangzhou (CN); Qi Zhang, Hangzhou (CN); Yuan Wang, Hangzhou (CN); Pengyun Liu, Hangzhou (CN); Baoyu Han, Hangzhou (CN); Huafen Liu, Hangzhou (CN)

(73) Assignee: Hangzhou Calibra Diagnostics Co., Ltd., Hangzhou (CN)

( * ) Notice: Subject to any disclaimer, the term of this patent is extended or adjusted under 35 U.S.C. 154(b) by 68 days.

(21) Appl. No.: 17/238,652

(22) Filed: Apr. 23, 2021

(65) Prior Publication Data

US 2022/0317137 A1 Oct. 6, 2022

(51) Int. Cl.
*G01N 33/82* (2006.01)
*G01N 1/40* (2006.01)
*G01N 30/06* (2006.01)
*G01N 30/04* (2006.01)

(52) U.S. Cl.
CPC .......... *G01N 33/82* (2013.01); *G01N 1/4044* (2013.01); *G01N 2001/4061* (2013.01); *G01N 2030/045* (2013.01); *G01N 2030/062* (2013.01); *Y10T 436/107497* (2015.01)

(58) Field of Classification Search
CPC ............. G01N 33/82; G01N 1/4044; G01N 2001/4061; G01N 2030/045; G01N 2030/062; G01N 2001/2893; Y10T 436/107497
See application file for complete search history.

(56) References Cited

FOREIGN PATENT DOCUMENTS

CN 111999397 A * 11/2020
WO WO-2019155057 A2 * 8/2019 ............. G01N 30/06

OTHER PUBLICATIONS

Midttun, O. et al. "Determination of vitamins A, D and E in a small volume of human plasma by a high-throughput method based on liquid chromatography/tandem mass spectrometry," Rapid Commun. Mass Spectrom. 2011, 25, 1942-1948 (Year: 2011).*

* cited by examiner

*Primary Examiner* — Jennifer Wecker
*Assistant Examiner* — Michelle Adams
(74) *Attorney, Agent, or Firm* — NZ CARR LAW OFFICE (57) ABSTRACT

The present invention describes a test kit for the detection of fat-soluble vitamins in serum using a method based on high performance liquid chromatography coupled with tandem mass spectrometry (HPLC-MS/MS). The internal standard (IS) solution included in the kit is based on methanol, acetonitrile and isopropyl alcohol solvents. Ammonium acetate is added to the IS solution to make it more stable and last for longer storage time. The application of this kit can significantly improve the recovery and detection sensitivity of vitamins A, E, K1 and K2 in serum without additional sample enrichment, make sample preparation process simpler and more efficient, keep processed samples stable for longer time, and lower the overall cost for more accurate and repeatable test results.

6 Claims, 5 Drawing Sheets

TEST KIT FOR TESTING FAT-SOLUBLE VITAMINS IN SERUM USING HIGH PERFORMANCE LIQUID CHROMATOGRAPHY COUPLED WITH TANDEM MASS SPECTROMETRY

CROSS-REFERENCE TO RELATED APPLICATIONS

The present invention claims priority of two prior Chinese application: film g No: 2021102411427 and filing No: 2021102411501, both of which are filed on Mar. 4, 2021, which are hereby incorporated in their entireties including embodiments, figures and claims.

BACKGROUND OF THE INVENTION

Field of the Invention

The current invention is in the field of analytical chemistry. Specifically, it relates to a test kit and a method for detecting fat-soluble vitamins in serum.

Description of the Related Art

Vitamins play important roles in health. Vitamin A, also known as retinol, functions in maintaining normal vision, epithelial tissue, and promoting healthy growth and development of bones. Insufficient vitamin A can lead to nutritional deficiencies such as dry eye, night blindness and hyperkeratosis. 25-Hydroxyvitamin D is an important factor in the regulation of calcium and phosphorus metabolism in human body. It coordinates mobilization and deposition of calcium in bone, regulates absorption and excretion of calcium through the urinary system, stabilizes calcium level in blood, and thus is important in bone development, muscular nerve conduction, normal cellular activities and signal transduction. Deficiency of 25-Hydroxyvitamin D can cause rickets in children and osteomalacia or osteoporosis in adults; excessive 25-Hydroxyvitamin D can cause increased absorption of calcium, leading to hypercalcemia. Vitamin E is a group of tocopherols that exist as stereoisomers, of which α-tocopherol has the strongest activity. Vitamin E promotes sex hormone secretion to improve fertilities of both men and women, keeps cell membrane from damaging effects of free radicals and oxidants, and prevents atherosclerosis, cardiovascular diseases and menopausal syndrome. Deficiency of vitamin E can cause testicular atrophy, degeneration of epithelial cells and abnormal gestation. The main physiological role of vitamin K is to participate in the synthesis of prothrombin and coagulation factors. Lack of vitamin K in human will lead to prolonged blood clotting time or hemorrhage in severe cases. Under the influence of certain factors (such as infection, diarrhea, etc.), there may even be risk of intracranial hemorrhage. Vitamin K1 is a substance necessary for liver to synthesize clotting factors II, VII, IX, and X. It is clinically used in the prevention and treatment of hypothrombin syndrome, vitamin K1 deficiency, neonatal spontaneous hemorrhage, as well as bleeding caused by obstructive jaundice, biliary fistula, and chronic diarrhea. Hypoprothrombinemia caused by coumarins, sodium salicylate can also be treated with vitamin K1. Vitamin K2 is the biologically active form of vitamin K and used in treatment of hemorrhagic disease caused by vitamin K deficiency. It can accelerate blood clotting process and prolong clotting time. Treatment of other health conditions using vitamin K2 are also reported. In summary, detecting these fat-soluble vitamins in human body can be used as a companion diagnostic to help doctors assess nutritional status of patients, make clinical decision and evaluate disease management and prognosis.

At present, there are many reported methods about testing fat-soluble vitamins in serum, both in China and internationally. Commonly used methods include chromatography, spectrophotometry, gas chromatography, liquid chromatography, etc. Among them, liquid chromatography or liquid chromatography coupled with tandem mass spectrometry is the preferred method for the determination of fat-soluble vitamins. These two methods can encounter problems such as complicated operational process, long analysis time, interfering factors in samples, poor specificity, low sensitivity, poor qualitative and quantitative accuracy, and poor reproducibility. These problems are mostly due to cumbersome sample processing steps, low recovery rate and poor stability of test substances in sample preparation.

Most current sample extraction and purification methods for fat-soluble vitamins use liquid-liquid extraction (such as CN106504947A) or solid-liquid extraction (such as CN110763788A). Both require multiple operational steps such as dilution, repeated extraction, rotary evaporation, drying under nitrogen, and purification. The whole process is cumbersome and labor intensive. Liquid-liquid extraction is difficult to be adapted to automation for high throughput sample processing; solid-liquid extraction can be adapted to automation but its requirement of SLE plates increases the test cost.

Sample preparation by protein denaturing and precipitation have also been reported for determining fat-soluble vitamins in serum and plasma, and many related patent applications have been filed, such as CN111999397A and CN110487943B. However, protein denaturing and precipitation method is generally accompanied by low target recovery rate, leading to low test sensitivity. Some protein denaturing and precipitation methods even require further extraction steps after protein precipitation, which are laborious and hampering their application in clinical test.

Therefore, a sample preparation method for detection of fat-soluble vitamins which has the characteristics of simple processing, high efficiency, low cost and low labor is highly demanded. The method should be able to solve some of the current issues related to detection of fat-soluble vitamins using liquid chromatography coupled with tandem mass spectrometry and improve test sensitivity, result accuracy and repeatability.

BRIEF SUMMARY OF THE INVENTION

To solve some traditional questions in sample preparation for testing of fat-soluble vitamins, the present invention introduces a new test kit and detection method based on high performance liquid chromatography coupled with tandem mass spectrometry (HPLC-MS/MS) for fat-soluble vitamins in serum. The internal standard (IS) solution in the kit is prepared in methanol, acetonitrile and isopropyl alcohol. Also included in the IS solution is ammonium acetate. The kit enables simple and efficient sample extraction without the need of any sample enrichment, thus improves recovery and test sensitivity of fat-soluble vitamins in serum significantly. The IS solution is very stable for a long time, making each kit last longer and lowering test cost. Detection of fat-soluble vitamins using this kit is simple, convenient, and high efficient, resulting in accurate test results.

The present invention provides a test kit and related test method based on HPLC-MS/MS for analyzing fat-soluble vitamins in serum. IS solution included in the kit contains protein denaturing agents which are methanol, acetonitrile and isopropyl alcohol.

In some embodiments, the kit further contains calibration solution, quality control solution, liquid chromatography mobile phase solution and other consumables.

In some embodiments, fat-soluble vitamins referred in the present invention are one or more of vitamin A, 25-OH vitamin D2, 25-OH vitamin D3, vitamin E, vitamin K1 and vitamin K2. The abovementioned six vitamins are tested by HPLC-MS/MS and divided into groups based on retention time similarity. Mass spectrometry data collection is conducted in different time periods to improve test sensitivities for vitamin K1 and K2.

In traditional sample preparation methods for HPLC-MS/MS test, IS solution and sample extraction reagents, such as protein denaturing agents, are separated and need to be added to samples in two steps. That increases both processing time and labor.

After multiple tests by our research group, we were surprised to discover that by mixing methanol, acetonitrile and isopropyl alcohol, as protein denaturing agents, into IS solution; the mixture can be added directly to samples for sample extraction and purification without affecting the functions of internal standards. The new IS solution has high selectivity and solubility for fat-soluble vitamins, making it unnecessary to perform additional sample enrichment processes such as lyophilizing, liquid-liquid extraction and nitrogen gas drying. After protein denaturation and precipitation in the IS solution, the supernatant containing target vitamins can be injected directly. All these improvements make sample preparation more easily and increase test sensitivity. Test cost is also reduced since methanol, acetonitrile and isopropyl alcohol as they are the routine laboratory solvents that are inexpensive.

After rigorous stability test, it was found that the new IS solution with methanol, acetonitrile and isopropyl alcohol is very stable, making it convenient for instant application and long term storage.

In some embodiments, the IS solution also contains additives including one or more of formic acid, ammonium fluoride, ammonium formate, ammonium acetate, and 2,6-di-tert-butyl-4-methylphenol.

Adding these additives to the IS solution as above can exert a synergistic effect and further improve the recovery of fat-soluble vitamins from the serum samples.

In some embodiments, the additive to the IS solution is ammonium acetate. The IS solution contains internal standards of the fat-soluble vitamins to be tested.

We found that the synergistic effect is the most obvious when the additive is ammonium acetate, which generates the highest recovery rate for fat-soluble vitamins in serum samples.

In some embodiments, the volume ratio of methanol to acetonitrile to isopropyl alcohol is 5-75%: 5-75%: 5-75%, and the concentration of ammonium acetate is 10-50 mM.

In some embodiments, the volume ratio of methanol to acetonitrile to isopropyl alcohol is 70-75%:15-25%:5-10%, and the concentration of ammonium acetate is 40-50 mM.

In some embodiments, the volume ratio of 40-50 mM ammonium acetate to methanol/acetonitrile/isopropyl alcohol (70-75%:15-25%:5-10%) is 1:124 in the IS solution, which also contains one or more of VA1-d6, 25-OH VD3-d6, 25-OH VD2-d6, VK1-d4 and VE-d6. VA1-d6 is the stable isotope labelled internal standard for vitamin A, 25-OH VD3-d6 is the stable isotope labelled internal standard for 25-OH vitamin D3, 25-OH VD2-d6 is the stable isotope labelled internal standard for 25-OH vitamin D2, VK1-d4 is the stable isotope labelled internal standard for vitamin K1 and K2, and VE-d6 is the stable isotope labelled internal standard for vitamin E.

It has been demonstrated repeatedly in tests that the newly formulated IS solution in the present invention is stable for over two years at room temperature.

The recipes and ratios of additives in the IS solution described in the present invention make great contributions to the increased selectivity and solubility of fat-soluble vitamins, as well as contribute to the increased test sensitivities.

In some embodiments, the kit contains consumable of low adsorption 96-well plates.

In some embodiments a calibration solution is also included in the kit, and the calibration solution, also called as a standard solution, is: one or more standard (perdetermined concentration) of vitamin A, 25-OH vitamin D2, 25-OH vitamin D3, vitamin E, vitamin K1 and vitamin K2 at standard concentrations is added to blank human serum.

The quality control sample is prepared in human serum matrix at three different concentrations.

Liquid chromatography mobile phase solution A and B are provided. A is 0.1% formic acid in water and B is 0.1% formic acid in methanol.

In some embodiments, high test sensitivity can be achieved when liquid chromatography mobile phase solution A is 0.1% formic acid in water and B is 0.1% formic acid in methanol. When starting from 50 µL serum sample, the lowest concentration point in the standard curves of the six fat-soluble vitamins is well within commonly required limit of quantitation.

In some embodiments, the calibration solution is prepared by making one or more of serially diluted vitamin A, 25-OH vitamin D2, 25-OH vitamin D3, vitamin E, vitamin K1 and vitamin K2 standard solutions in blank human serum matrix. In some embodiments, the quality control solution is prepared by mixing one or more of vitamin A, 25-OH vitamin D2, 25-OH vitamin D3, vitamin E, vitamin K1 and vitamin K2 standard solutions at low, medium and high concentrations with human serum matrix.

The usage of blank human serum matrix (no targeted analyte) in the calibration solution and human serum matrix in quality control solution decreases matrix effect in the test of fat-soluble vitamins in human serum samples while increasing accuracy and reliability of the standard curve of analysis.

In addition, the present invention provides a method for detecting fat-soluble vitamins in serum by HPLC-MS/MS. The method adopts the above-mentioned test kit for sample extraction, purification, and target detection which includes the following steps: 50 µL of each sample is added to a 96-well plate, 150-350 µL IS solution (as described above) is then added to each sample and mixed thoroughly by vortexing at a speed of 600-1000 rpm for 10 minutes; the plate is then centrifuged; 200 µL of supernatant is transferred to a 96-well low adsorption plate and ready for analysis.

This method in the current invention only requires small volume of samples at 50 µL each, which is friendly to clinical sample collection wherein it is difficult to collect large amount of blood samples sometimes.

For sample preparation, the volume ratio of sample to internal standard solution is 1:3 to 1:7.

The usage of a low adsorption 96-well plate for sample injection reduces risk of fat-soluble vitamins being adsorbed in sample wells, thus improving the precision and accuracy of test results.

A large number of tests have proved that the combination of the optimized IS solution and a low-adsorption sample plate can reduce the risk of target substances being adsorbed on the sample plate, improve the stability of extracted fat-soluble vitamins, and ensure high precision and accuracy of test results.

In some embodiments, the volume of the IS solution in the kit is 250 µL.

In some embodiments, the sample detection method includes the application of liquid chromatography with gradient elution, tandem mass spectrometry, atmospheric pressure chemical ionization (APCI), positive ion multiple reaction monitoring scan (MRM), and segmented data collection based on retention time.

Furthermore, the time of the gradient elution is seven minutes and the gradient elution program is as following:

| time (min) | Mobile phase A % | Mobile phase B % | Flow rate (ml/min) |
|---|---|---|---|
| 0.00 | 60.0 | 40.0 | 0.70 |
| 4.50 | 10.0 | 90.0 | 0.70 |
| 5.00 | 0.0 | 100.0 | 0.70 |
| 6.70 | 0.0 | 100.0 | 0.70 |
| 6.71 | 60.0 | 40.0 | 0.70 |
| 7.00 | 60.0 | 40.0 | 0.70 |

Using the above gradient elution program, interference of serum matrix to the detection of the six fat-soluble vitamins is minimized, and all six fat-soluble vitamins can be well separated in liquid chromatography, enabling simultaneous detection of all six fat-soluble vitamins through mass spectrometry. The test time for a single sample is shortened to 7.0 minutes which increases the number of tested samples in unit time and lowers test cost. Wide reportable range and accurate test results of the six fat-soluble vitamins in serum are also achieved through this gradient elution program.

Furthermore, the high performance liquid chromatography parameters are: a C18 chromatographic column; flow rate of the mobile phase is 0.70 mL/min; and the column temperature is 40° C.

Furthermore, the mass spectrometry parameters are:

| Ionization mode | atmospheric pressure chemical ionization (APCI (+)) | Scan Mode | Multiple reaction monitoring (MRM) |
|---|---|---|---|
| Spray voltage | 4500 V | Temperature | 450° C. |
| GS1 (Ion source gas) | 50 L/min | GS2 (auxiliary gas) | 50 L/min |
| Curtain gas | 30 L/min | / | / |

Furthermore, the mass over charge (m/z) ratio of parent ion/product ion pairs (Q1/Q3) monitored in mass spectrometer for the six fat-soluble vitamins and their stable isotope labelled internal standards are:

| Analyte/Internal standard | Q1 | Q3 |
|---|---|---|
| Vitamin A | 269.2 | 119.1 |
|  | 269.2 | 93.0 |
| 25-OH vitamin D2 | 395.3 | 271.1 |
|  | 413.3 | 271.1 |
| 25-OH vitamin D3 | 383.3 | 257.2 |
|  | 401.3 | 257.2 |
| Vitamin E | 431.4 | 137.1 |
|  | 431.4 | 109.0 |
| Vitamin K1 | 451.3 | 187.1 |
|  | 451.3 | 225.1 |
| Vitamin K2 | 445.2 | 187.2 |
|  | 445.2 | 81.1 |
| Vitamin A-d6 | 275.3 | 122.1 |
|  | 275.3 | 96.0 |
| 25-OH vitamin D2-d3 | 398.3 | 274.1 |
|  | 416.3 | 274.1 |
| 25-OH vitamin D3-d6 | 389.3 | 263.2 |
|  | 407.3 | 263.2 |
| Vitamin E-d6 | 437.4 | 143.1 |
|  | 437.4 | 115.1 |
| Vitamin K1-d4 | 455.4 | 191.1 |
|  | 455.4 | 229.1 |

In some embodiments, the segmented data collection program is: vitamin A, 25-OH vitamin D2, and 25-OH vitamin D3 are in the first group; vitamin E, vitamin K1 and vitamin K2 are in the second group. Alternatively, vitamin A, 25-OH vitamin D2, 25-OH vitamin D3 and vitamin E are put in the first group, vitamin K1 and vitamin K2 are still in the second group.

In some embodiments, the method also describes data analysis which includes making standard curve, calculating target recovery rate, evaluating matrix effect and method precision, and calculating actual concentrations of fat-soluble vitamins in the tested human serum samples.

In another aspect, the present invention provides the use of ammonium acetate in preparing IS solution. The IS solution containing ammonium acetate is used for preparing samples that are going to be analyzed by HPLC-MS/MS to detect fat-soluble vitamins in serum.

Furthermore, the fat-soluble vitamins are one or more of vitamin A, 25-OH vitamin D2, 25-OH vitamin D3, vitamin E, vitamin K1 and vitamin K2.

The present invention brings the following advantages:

(1) The IS solution described in the present invention is a new type of internal standard solution which not only plays the role of internal standard but also serves in sample extraction and purification. The new IS solution has high selectivity and solubility for fat-soluble vitamins, especially for vitamin A, vitamin E, vitamin K1, and vitamin K2. It also eliminates the need of sample enrichment processes such as lyophilizing or drying under nitrogen after liquid-liquid extraction. After sample extraction using this IS solution, the extract is centrifuged and the supernatant can be used directly for sample injection, thus greatly simplifying sample preparation process and test sensitivity.

(2) The reagents used in the IS solution described in the current invention is made from inexpensive routine chemicals and thus reduces test cost.

(3) The IS solution described in the present invention is very stable and can be stored for a long time, making the test process more convenient and efficient.

(4) On the basis of the optimized IS solution, the use of a low adsorption sample plate further reduces the risk of target analytes being adsorbed to the plate, improves the stability of fat-soluble vitamins after extraction, and ensures precision and accuracy of test results.

(5) By preparing the calibration solution and quality control solution in human serum reduces sample matrix effect and improves accuracy and reliability of the standard curve.

(6) The use of mobile phase A (0.1% formic acid in water) and mobile phase B (0.1% formic acid in methanol) in the current invention ensures high sensitivity of the test.

(7) The run time of each sample is shortened to seven minutes using the HPLC-MS/MS method in the present invention, which helps reducing cost. Using the optimized gradient elution program ensures good separation of target vitamins in liquid chromatography and simultaneous detection of all six fat-soluble vitamins in one injection. The detection sensitivity of vitamin K1 and K2 is further improved by utilizing mass spectrometry and segmented data collection in mass spectrometry.

(8) The serum sample volume required is small at 50 μL only, which is friendly to clinical blood collection.

(9) The method in the present invention has wide reportable range which ensures accurate detection of the six fat-soluble vitamins in serum.

(10) The detection sensitivities for vitamin A, 25-OH vitamin D2, 25-OH vitamin D3, vitamin E, vitamin K1 and vitamin K2 can reach 0.4 ng/mL, 0.7 ng/mL, 0.3 ng/mL, 3 ng/mL, 10 pg/ml and 6 pg/mL, respectively.

BRIEF DESCRIPTION OF THE DRAWINGS

Note: The concentration of each vitamin in the FIGS. 1A-1E is the lowest concentration (S1) of each serially diluted vitamin standard dissolved in blank human serum.

DETAILED DESCRIPTION OF THE INVENTION

The present invention will be further described in detail below with reference to the accompanying figures and embodiments or samples. It should be pointed out that the embodiments described below are intended to facilitate the understanding of the present invention and do not have any limiting on the claims. The reagents used in the following embodiments are all commercially available products that can be purchased.

Embodiment #1: Sample Preparation, Detection and Data Analysis

Sample Preparation
1. Preparation of Standard Solutions and Quality Control Solutions Vitamin A, 25-hydroxyvitamin D2, 25-hydroxyvitamin D3, vitamin E, vitamin K1, and vitamin K2 standard solutions are mixed to make a stock solution. Standard solution and quality control solution are diluted from the stock solutions and mixed with blank human serum (without fat-soluble vitamins) or human serum at a volume ratio of 1:49, respectively.

Each of the six fat-soluble vitamins has 10 serially diluted concentrations in the standard solution (S1-S10), which are specified in table 1.

TABLE 1

10 serially diluted concentrations (S1-S10) of the six fat soluble vitamin in standard curve

| ng/ml | Vitamin A | 25-OH Vitamin D2 | 25-OH Vitamin D3 | Vitamin E | Vitamin K1 | Vitamin K2 |
|---|---|---|---|---|---|---|
| S1 | 40 | 2 | 3 | 500 | 0.10 | 0.10 |
| S2 | 60 | 3 | 4.5 | 750 | 0.15 | 0.15 |
| S3 | 100 | 5 | 7.5 | 1250 | 0.25 | 0.25 |
| S4 | 160 | 8 | 12 | 2000 | 0.40 | 0.40 |
| S5 | 200 | 10 | 15 | 2500 | 0.50 | 0.50 |
| S6 | 400 | 20 | 30 | 5000 | 1.00 | 1.00 |
| S7 | 600 | 30 | 45 | 7500 | 1.50 | 1.50 |
| S8 | 1000 | 50 | 75 | 12500 | 2.50 | 2.50 |
| S9 | 1600 | 80 | 120 | 20000 | 4.00 | 4.00 |
| S10 | 2000 | 100 | 150 | 25000 | 5.00 | 5.00 |

In the quality control solutions, each of the six fat-soluble vitamins has three concentrations: low, medium, and high, which are specified in table 2.

TABLE 2

Three concentrations of the six fat-soluble vitamins in quality control solutions

| ng/ml | Vitamin A | 25-OH Vitamin D2 | 25-OH Vitamin D3 | Vitamin E | Vitamin K1 | Vitamin K2 |
|---|---|---|---|---|---|---|
| Low | 144 | 7.2 | 10.8 | 1800 | 0.36 | 0.36 |
| Medium | 480 | 24.0 | 36.0 | 6000 | 1.20 | 1.20 |
| High | 1440 | 72.0 | 108.0 | 18000 | 3.60 | 3.60 |

2. Preparation of Internal Standard (IS) Solutions
(1) Preparation of the Internal Standard Solutions The concentrations of the internal standard solutions of Vitamin A-d6, 25-OH Vitamin D2-d3, 25-OH Vitamin D3-d6, vitamin E-d6, and vitamin K-d4 are 3.0 μg/mL, 1.0 μg/mL, 1.0 μg/mL, 20 μg/mL, and 0.025 μg/mL in methanol, respectively.

(2) Preparation of the Internal Standard Solutions

Mix 750 ml methanol, 150 ml acetonitrile, and 100 ml isopropyl alcohol to make a 75:15:10 methanol/acetonitrile/isopropyl alcohol mixture; weigh 3.85 g ammonium acetate and add it to the above mixture to make solution A, which is 50 mM ammonium acetate in 75% methanol, 15% acetonitrile and 10% isopropyl alcohol.

Transfer 2 ml internal standard solution to 248 ml solution A (v/v 1:124).

Although ammonium acetate is used in this embodiment, it has been demonstrated repeatedly that formic acid, ammonium fluoride, ammonium formate, or 2,6-di-tert-butyl-4-methylphenol can also be used in place of ammonium acetate, which will exert the synergistic effect in elevating the recovery rate of the six fat-soluble vitamins in human serum samples.

Sample Processing

Human serum sample, standard solution, and quality control solutions are processed in the same manner as following:

(1) Transfer 50 μL of each above solution (Human serum sample, standard solution, and quality control solutions) into one well of the wells of a 96-deepwell plate (2) Add 250 μL IS solution to the same well and vortex the plate to mix at 1000 rpm for 10 minutes.

(3) Spin the plate in a centrifuge at 4,000 rpm for 10 minutes, transfer 200 μL of the supernatant to a new low adsorption 96-well plate and wait to be tested.

Sample Analysis

Inject 40 μL of each processed extract (step (3)) into the HPLC-MS/MS system using the following setting:

Mass spectrometer: AB SCIEX Triple Quad 4500MD; chromatographic column: Phenomenex Luna C18 (3 μm, 50×2.0 mm); mobile phase solution A: 0.1% formic acid in water; mobile phase solution B: 0.1% formic acid in methanol; chromatographic flow rate: 0.7 mL/min; column temperature: 40° C.; injector temperature: 15° C.; injection volume: 40 μL.

Gradient elution program is detailed in table 3.

TABLE 3

Gradient elution program

| time (min) | Mobile phase A % | Mobile phase B % | Flow rate (ml/min) |
| --- | --- | --- | --- |
| 0.00 | 60.0 | 40.0 | 0.70 |
| 4.50 | 10.0 | 90.0 | 0.70 |
| 5.00 | 0.0 | 100.0 | 0.70 |
| 6.70 | 0.0 | 100.0 | 0.70 |
| 6.71 | 60.0 | 40.0 | 0.70 |
| 7.00 | 60.0 | 40.0 | 0.70 |

The retention times of the six fat-soluble vitamins are: 2.84 minutes for vitamin A, 2.75 minutes for 25-OH vitamin D2, 2.69 minutes for 25-OH vitamin D3, 5.03 minutes for vitamins E and K2, and 5.69 minutes for vitamin K1.

Figure 1A:
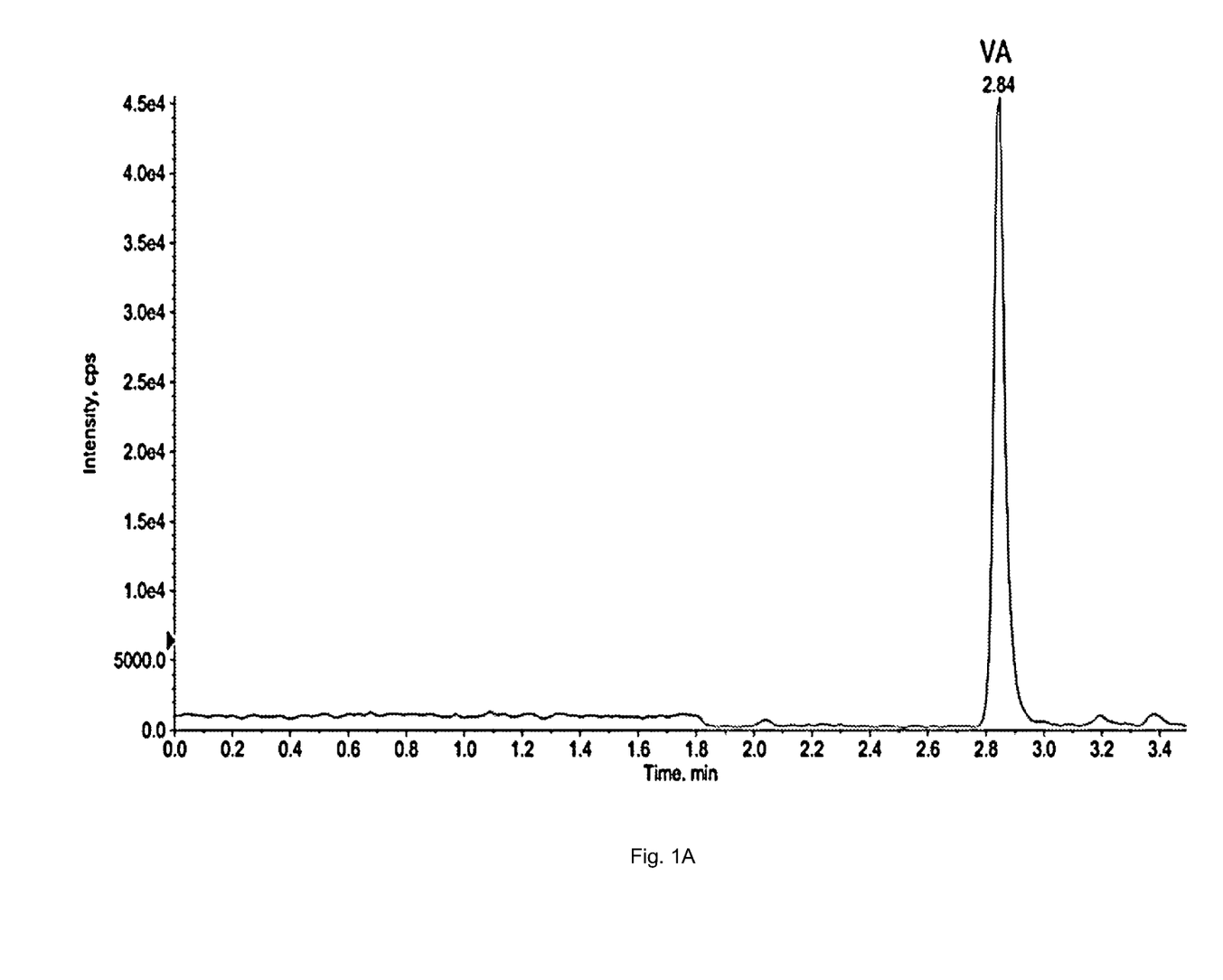
FIG. 1A is the chromatographs of the vitamin A analyzed in embodiment 1.
Figure 1B:
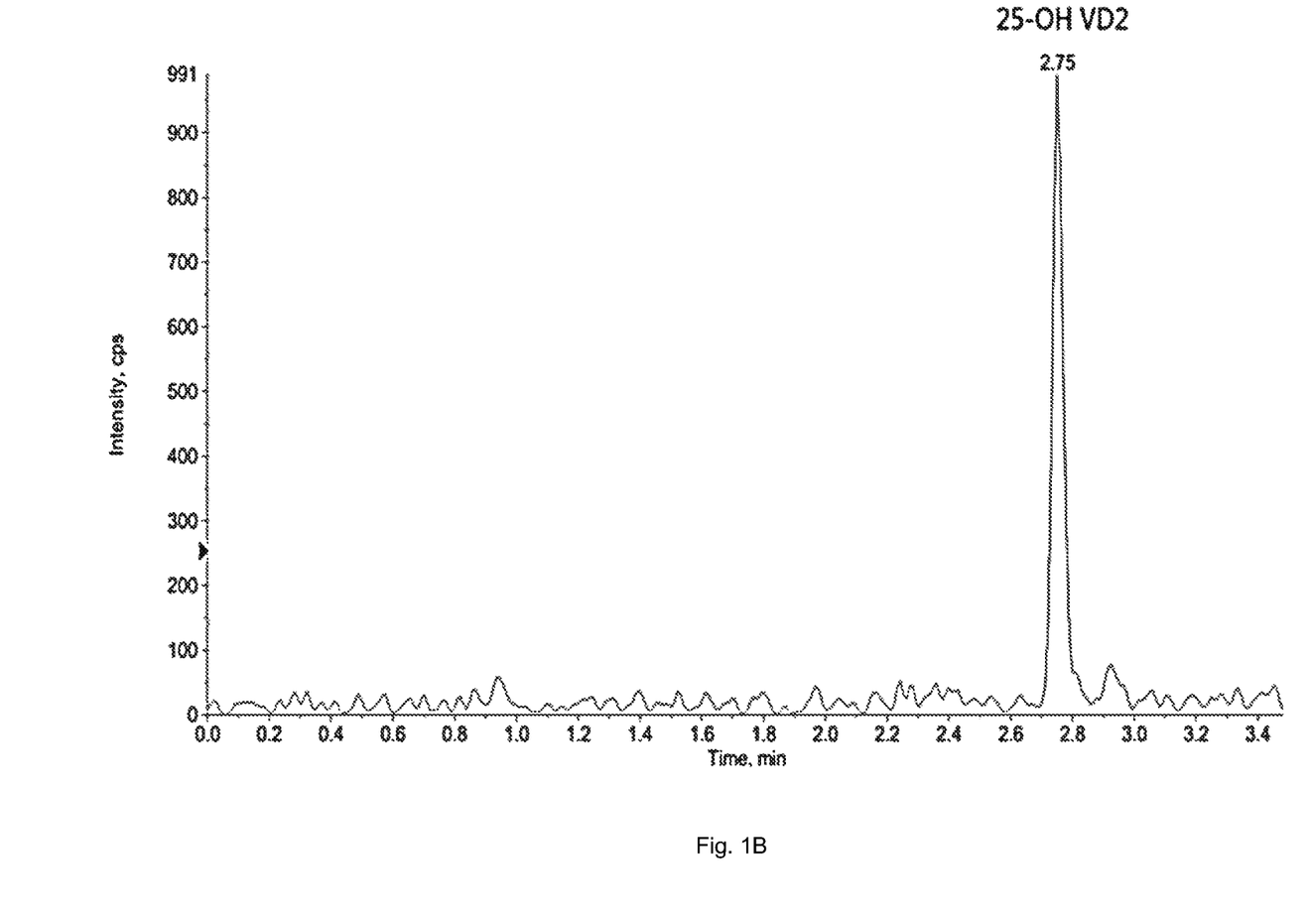
FIG. 1B is the chromatographs of the 25-OH vitamin D2 analyzed in embodiment 1.
Figure 1C:
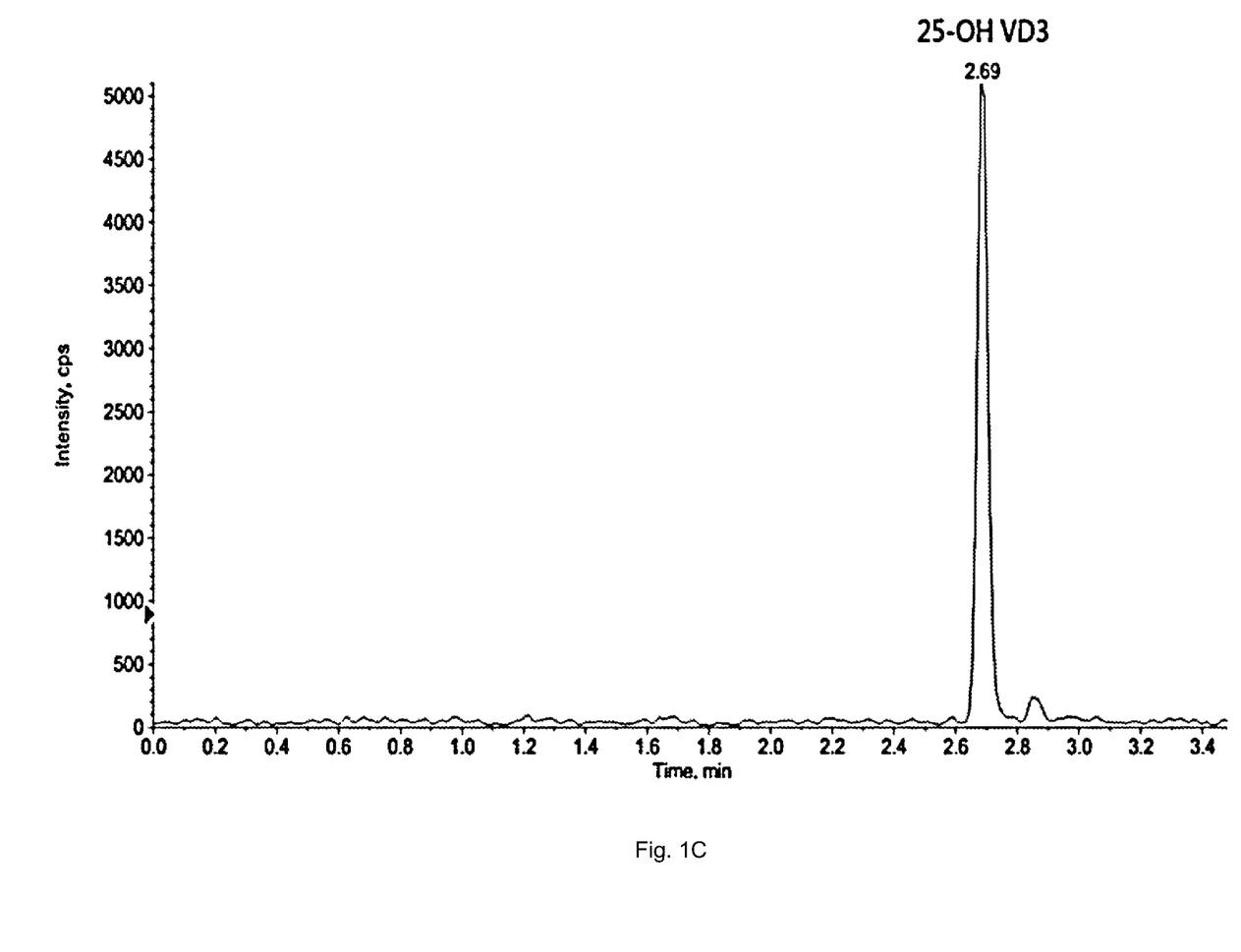
FIG. 1C is the chromatographs of the 25-OH vitamin D3 analyzed in embodiment 1.
Figure 1D:
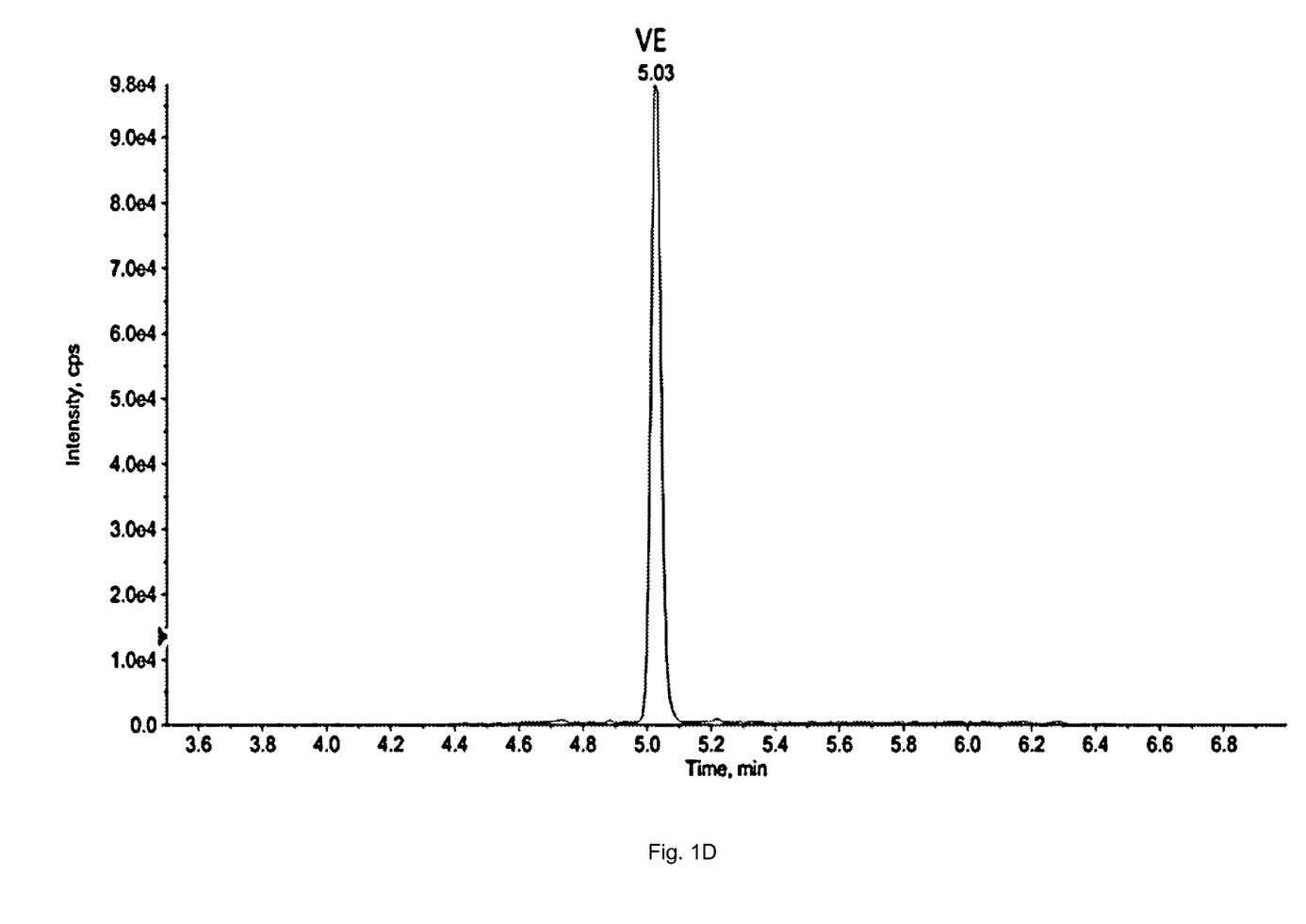
FIG. 1D is the chromatographs of the vitamin E analyzed in embodiment 1.
Figure 1E:
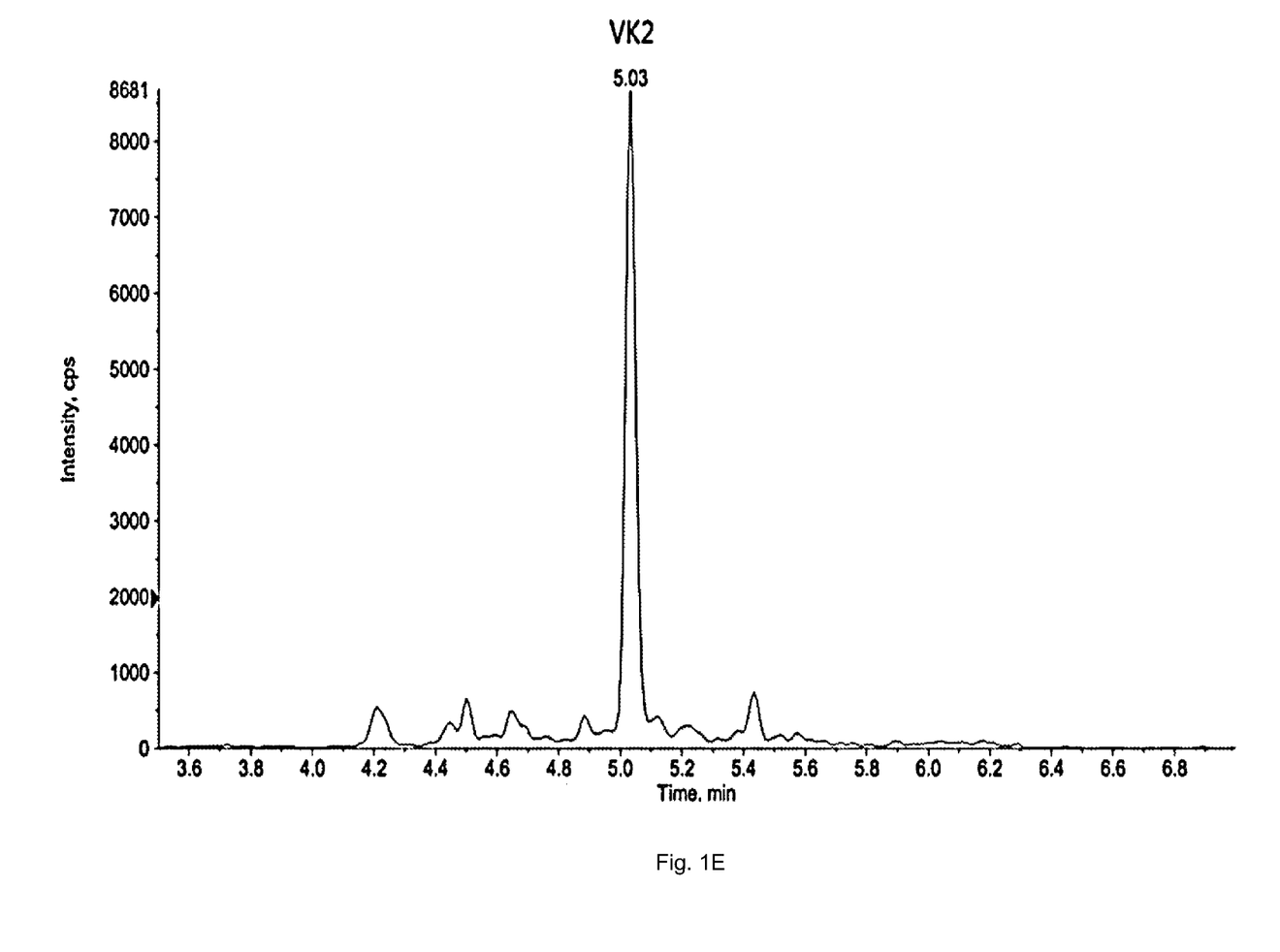
FIG. 1E is the chromatographs of the vitamin K2 analyzed in embodiment 1.

As illustrated in FIG. 1A-1E, the six vitamins are separated after liquid chromatography and eluted at different retention times into mass spectrometer, in which each vitamin is detected by selected ion monitoring and its concentration is determined.

The six fat-soluble vitamins separated through liquid chromatography are eluted into a mass spectrometer for detection. Atmospheric pressure chemical ionization (APCI) and multiple reaction monitoring (MRM) scan mode are used to detect the six fat-soluble vitamins. A standard curve is also made to calculate the concentrations of the six vitamins.

Segmented data collection in mass spectrometer is as following: the first segment includes vitamin A, 25-OH-vitamin D2, and 25-OH-vitamin D3; the second segment includes vitamin E, vitamin K1, and vitamin m2.

The parameters of the mass spectrometer are detailed in table 4.

TABLE 4

Parameters of the mass spectrometer

| Ionization mode | APCI (+) | Scan Mode | MRM |
| --- | --- | --- | --- |
| Spray voltage | +4500 V | temperature | 450° C. |
| Sheath gas | 50 L/min | Auxiliary gas | 50 L/min |
| Curtain gas | 30 L/min | data collection segment | first: 0-3.5 min second: 3.5-7 min |

The m/z of parent/product ion pair, declustering potential (DP), collision energy (CE), and collision cell exit potential CXP) for detecting each vitamin is listed in Table 5.

TABLE 5

Parent/product pair m/z and other parameters

| Analyte and internal standard | Q1 m/z | Q3 m/z | DP | CE | CXP |
| --- | --- | --- | --- | --- | --- |
| Vitamin A | 269.2 | 119.1 | 59 | 25 | 11 |
|  | 269.2 | 93.0 | 66 | 34 | 11 |
| 25-OH vitamin D2 | 395.3 | 271.1 | 70 | 19 | 11 |
|  | 413.3 | 271.1 | 70 | 19 | 11 |
| 25-OH vitamin D3 | 383.3 | 257.2 | 103 | 21 | 11 |
|  | 401.3 | 257.2 | 68 | 22 | 11 |
| Vitamin E | 431.4 | 137.1 | 80 | 60 | 11 |
|  | 431.4 | 109.0 | 83 | 61 | 11 |
| Vitamin K1 | 451.3 | 187.1 | 92 | 34 | 11 |
|  | 451.3 | 225.1 | 73 | 27 | 11 |
| Vitamin K2 | 445.2 | 187.2 | 75 | 29 | 11 |
|  | 445.2 | 81.1 | 75 | 29 | 11 |
| Vitamin A-d6 | 275.3 | 122.1 | 51 | 30 | 11 |
|  | 275.3 | 96.0 | 68 | 32 | 11 |
| 25-OH vitaminD2-d3 | 398.3 | 274.1 | 70 | 16 | 11 |
|  | 416.3 | 274.1 | 69 | 16 | 11 |
| 25-OH vitaminD3-d6 | 389.3 | 263.2 | 72 | 21 | 11 |
|  | 407.3 | 263.2 | 43 | 21 | 11 |
| Vitamin E-d6 | 437.4 | 143.1 | 66 | 62 | 11 |
|  | 437.4 | 115.1 | 77 | 70 | 11 |
| Vitamin K-d4 | 455.4 | 191.1 | 92 | 31 | 11 |
|  | 455.4 | 229.1 | 97 | 27 | 11 |

The fat-soluble vitamins are detected by selecting corresponding ion pairs in selected reaction monitoring at specified retention time, and quantified by using corresponding internal standards.

After being separated by liquid chromatography, different fat-soluble vitamins are eluted at different retention times, detected and quantified using multiple reaction monitoring mode of the mass spectrometer. Serially diluted internal standard solutions are mixed with reference blank human serum and analyzed the same as for samples.

FIG. 1A-1E demonstrates a typical chromatography of detection of the six fat-soluble vitamins, which shows that using the method described in the present invention can detect all six fat-soluble vitamins simultaneously and accurately.

Data Processing and Analysis

1. Making Standard Curve

The standard curve is made by plotting the ratio of a target vitamin's peak area to its internal standard's peak area on the y-axis against the known concentration of the internal standard on the x-axis for linear regression analysis. The linear regression equation and correlation coefficient (r) are listed in Table 6.

TABLE 6

Standard curve linear regression equations and correlation coefficients

| Analyte | linear regression equations and correlation coefficients |
| --- | --- |
| Vitamin A | y = 0.05055*x + 0.09145 (r = 0.99845) |
| 25-OH vitamin D2 | y = 0.04916*x + 0.1723 (r = 0.99906) |
| 25-OH vitamin D3 | y = 0.05218*x + 0.27584 (r = 0.99920) |
| Vitamin E | y = 0.04822*x + 0.13845 ( r = 0.99898) |
| Vitamin K1 | y = 0.05207*x + 0.19085 (r = 0.99553) |
| Vitamin K2 | y = 0.05064*x + 0.2871 (r = 0.99721) |

2. Accuracy, Precision and Matrix Effect (1) Accuracy and Precision

The ratios of a target vitamin's peak area to its internal standard's peak area in low, medium and high concentration quality control solutions are determined. The ratios are input into the standard curve equation to calculate each vitamin's concentration in the quality control samples. The results from three repeated analyses are used to calculate accuracy and precision. The detected values are acceptable in accuracy when the average values of the three repeats are 85.0% to 115.0% of the actual values and covariance (CV) is:15%. Precision is acceptable when the tested values are within 91.2% to 110.5% in three repeated assays of the quality control solutions at all three concentrations. The CV value of 1.46% to 9.25% between different batches of test is accepted.

(2) Matrix Effect

The matrix effect is determined by comparing the concentration of a pure standard solution to the detected value when it is mixed with a blank matrix. When the detected value in a matrix is 85% to 115% of the value of the pure standard, the matrix effect is negligible. When a matrix effect is present, it should be consistent among the quality control samples at all three concentrations. It is acceptable when matrix factor normalized by internal standard is between 95%-106% and CV is between 1.75%-8.76%.

3. Calculation of the Concentrations of the Six Fat-Soluble Vitamins in Human Serum Samples The ratio of each vitamin's peak area to its internal standard's peak area in LC-MS/MS is calculated first, and the concentration of each vitamin in a serum sample is then calculated by input this ratio into the corresponding standard curve equation.

Embodiment 2: Stability Test of Internal Standard Solutions in Different Compositions Under Long Term Storage In this embodiment, internal standard solutions containing the isotope-labeled fat-soluble vitamins are prepared according to the method described in embodiment 1. The compositions of the tested internal standard solutions are listed in Table 7. Stability is evaluated by incubating internal standard solutions in 48° C. for six months and observing for turbidity and other abnormalities. After six months, the stored internal standard solution is tested and the result is compared to that from an identically but freshly prepared internal standard solution. The concentration of the internal standard solution used in the stability test is the lowest concentration point in the standard curve (S1). Since all six fat-soluble vitamins demonstrate similar test results, herein only the results form vitamin K1 is presented (Table 7).

TABLE 7

Stability test of internal standard solution in different solvent systems

| | solvent | observation | Deviation of vitamin K1-d4 concentration | Deviation of vitamin K1 recovery | Shelf life |
|---|---|---|---|---|---|
| 1 | 75% methanol/ 15% acetonitrile/ 10% isopropanol with 50 mM ammonium acetate | No abnormality | −0.6% | −1.1% | ≥2 years |
| 2 | 80% methanol/ 20% acetonitrile with 50 mM ammonium acetate | No abnormality | −37.2% | −7.3% | 3 months |
| 3 | 75% methanol/ 15% acetonitrile/ 10% isopropanol | No abnormality | −13.9% | −9.6% | 3 months |
| 4 | 80% methanol/ 20% acetonitrile | No abnormality | −65.2% | −10.5% | 1 week |
| 5 | methanol | No abnormality | −91.9% | −18.7% | 1 day (freshly made) |
| 6 | acetonitrile | No abnormality | −85.8% | −20.4% | 1 day (freshly made) |

The results in Table 7 demonstrate that the prepared internal standard solution is the most stable if it consists of ammonium acetate, methanol, acetonitrile and isopropyl alcohol at the same time. This internal standard solution behaves almost the same after six months storage at 48° C. and its shelf life can be as long as more than two years. When the internal standard solution consists of ammonium acetate, methanol and acetonitrile or methanol, acetonitrile and isopropyl alcohol, their stabilities after six months storage at 48° C. decrease significantly and resulting in significant deviation of the test result from the true value. When the internal standard solution contains only one or both of methanol and acetonitrile, its stability is poorer and the standard solution needs to be freshly prepared and used immediately, making sample preparation process cumbersome.

Thus, the internal standard solution described in the present invention proves to be very stable. By using this internal standard solution, traditionally separated sample extraction and adding internal standard solution steps can be combined into one single step, greatly simplifying sample preparation process. The internal standard solution can be prepared ahead of experiment and available whenever it is needed, which is quite convenient. Overall this is an optimized internal standard solution that greatly simplifies sample preparation process in clinical test of serum fat-soluble vitamins and has the potential to be widely adopted and applied.

Embodiment 3: Comparison of Fat-Soluble Vitamin Test Results Obtained by Using Internal Standard Solutions in Different Compositions In this embodiment, internal standard solutions containing isotope-labeled fat-soluble vitamins are prepared according to the method described in embodiment 1. The compositions of the tested internal standard solutions are listed in Table 8. The concentration of the tested internal standard solution is the lowest concentration point in the standard curve (S1). Samples preparation and analysis are carried out using methods described in embodiment 1. The test results of the six fat-soluble vitamins using internal standard solutions in different solvents are listed in Table 8.

TABLE 8

Test results using internal standard solutes in different solvents

| Internal standard solvents | Vitamin A | 25-OH vitamin D2 | 25-OH vitamin D3 | Vitamin E | Vitamin K1 | Vitamin K2 |
| --- | --- | --- | --- | --- | --- | --- |
| 75% methanol/ 15% acetonitrile/ 10% isopropanol with 50 mM ammonium acetate | 54672.9 | 1596.3 | 3514.9 | 56793.2 | 3480.9 | 6265.6 |
| 75% methanol/ 15% acetonitrile/ 10% isopropanol with 50 mM formate acetate | 51987.8 | 1357.4 | 3264.1 | 50318.7 | 2769.4 | 4874.1 |
| 75% methanol/ 15% acetonitrile/ 10% isopropanol with 50 mM 2,6-di-tert-butyl-4-methylphenol | 48758.3 | 1468.2 | 3307.8 | 49719.6 | 2708.5 | 4469.0 |
| 75% methanol/ 15% acetonitrile/ 10% isopropanol | 42780.4 | 1649.2 | 4107.5 | 40639.1 | 2058.7 | 3499.8 |
| 50% acetonitrile/ 50% isopropanol | 39244.8 | 2072.0 | 7084.4 | 35717.0 | 2054.5 | 3698.1 |
| 50% methanol/ 50% acetonitrile | 18902.5 | 982.8 | 3320.2 | 13644.0 | 1252.5 | 2254.5 |
| acetonitrile | 21776.5 | 1477.1 | 3979.1 | 39569.7 | 1172.9 | 1873.6 |
| methanol | 27287.9 | 1252.2 | 5603.3 | 31360.8 | 292.1 | 571.1 |

Conclusions can be drawn from the results in Table 8 that when using the solvent system recommended in the current invention (75% methanol/15% acetonitrile/10% isopropyl alcohol with 50 mM ammonium acetate), chromatographic peak areas of vitamin A, E, K1 and K2 are significantly increased. Although peak areas of 25-OH vitamin D2 and 25-OH vitamin D3 are slightly reduced, the test is friendly to low amount vitamins in human serum, such as vitamin K1 and K2, and is ideal when all six fat-soluble vitamins need to be analyzed at the same time.

The clinical reference range of vitamin K in human blood is only 0.13-1.39 ng/mL, thus a test method for vitamin K need to have high sample recovery rate and high test sensitivity. When testing all six fat-soluble vitamins at the same time, the test method should be optimized in favor of vitamin K. Although currently some methods for detecting multiple vitamins have been developed and reported, their recovery rate for vitamin K1 and K2 are not satisfactory, resulting in poor test sensitivity for vitamin K1 and K2 and makes it difficult to assess all six fat-soluble vitamins clinically.

The results in Table 8 also demonstrate that methanol has poor recovery for vitamin K and cannot meet the sensitivity requirement for testing clinical samples.

Using the combination of methanol and acetonitrile can improve the recovery of vitamin K significantly. Since the test substances are all fat-soluble vitamins, according to the rule of "likes dissolve likes", the introduction of isopropyl alcohol into the internal standard solution can further increase the recovery of vitamins A, E, K1, and K2. On the same basis, adding ammonium acetate, ammonium formate or 2,6-Di-tert-butyl-4-methylphenol can create significant synergistic effects. The synergistic effect from using ammonium acetate is particularly obvious, therefore the best solvent system for the internal standard solution is 50 mM ammonium acetate in 75% methanol/15% acetonitrile/10% isopropyl alcohol.

The internal standard solution described in this embodiment of the present invention not only simplifies sample preparation, but also significantly improves the recovery rate of vitamins A, E, and K (especially K1 and K2 which have the lowest amount among fat-soluble vitamins in human serum). Improved target recovery also means increased sensitivity and accuracy of the ensuing LC-MS/MS detection result, meeting requirement of each fat-soluble vitamin's clinical reference range. When using the optimized internal stand solution of 50 mM ammonium acetate in 75% methanol/15% acetonitrile/10% isopropyl alcohol for sample preparation, the sensitivities for vitamin A, 25-OH vitamin D2, 25-OH vitamin D3, vitamin E, vitamin K1 and vitamin K2 in subsequent LC-MS/MS detection are as low as 0.4 ng/mL, 0.7 ng/mL, 0.3 ng/mL, 3 ng/mL, 10 μg/ml and 6 μg/mL, respectively.

Embodiment 4: Effect of Different Solvent Ratios in Internal Standard Solution on LC-MS/MS Test Results In this embodiment, internal standard solutions containing isotope-labeled fat-soluble vitamins are prepared according to the method described in embodiment 1.

The internal standard solution contains ammonium, methanol, acetonitrile, and isopropyl alcohol. Different ratios of the four in the internal standard solution are tested (Table 9). The concentration of the internal standard is the lowest concentration point in the standard curve (S1). Sample preparation and analysis are carried out using the method described in embodiment 1. The test results of the six fat-soluble vitamins in internal standard solutions with different solvent ratios are listed in Table 9.

TABLE 9

Test results of the six fat-soluble vitamins in internal standard solutions with different solvent ratios

| Internal standard solution solvent system | Vitamin A | 25-OH vitamin D2 | 25-OH vitamin D3 | Vitamin E | Vitamin K1 | Vitamin K2 |
|---|---|---|---|---|---|---|
| 50 mM ammonium in 75% methanol/ 15% acetonitrile/ 10% isopropanol | 54672.9 | 1596.3 | 3514.9 | 56793.2 | 3480.9 | 6265.6 |
| 40 mM ammonium in 75% methanol/ 15% acetonitrile/ 10% isopropanol | 53791.6 | 1557.9 | 3764.7 | 55318.7 | 3269.4 | 5687.0 |
| 20 mM ammonium in 75% methanol/ 15% acetonitrile/ 10% isopropanol | 49287.9 | 1352.2 | 3003.9 | 50360.4 | 2992.1 | 4713.3 |
| 50 mM ammonium in 70% methanol/ 25% acetonitrile/ 5% isopropanol | 54180.8 | 1613.7 | 3507.2 | 56639.1 | 3398.5 | 5863.8 |
| 50 mM ammonium in 15% methanol/ 60% acetonitrile/ 25% isopropanol | 40245.7 | 2149.5 | 6389.8 | 36187.7 | 2134.6 | 4231.7 |
| 50 mM ammonium in 82% methanol/ 15% acetonitrile/ 3% isopropanol | 29385.1 | 1752.6 | 5517.5 | 31360.8 | 2098.1 | 3060.1 |
| 50 mM ammonium in 50% methanol/ 48% acetonitrile/ 2% isopropanol | 21902.4 | 1681.3 | 3816.4 | 24057.0 | 2151.5 | 2467.4 |

The results in Table 9 indicate that when the concentration of ammonium acetate in the internal standard solution is lowered to 20 mM, the recovery rate of fat-soluble vitamins will decrease, so the optimal concentration of ammonium acetate should be 40-50 mM. Similarly, when the percentage of methanol is increased to 80% or lowered to 15%, the recovery rates of fat-soluble vitamins also decrease. Too high or too low percentages of acetonitrile or isopropyl alcohol decrease the recovery of fat-soluble vitamins too. Therefore, based on extensive tests it is concluded that the optimal solvent system for internal standards should be 40-50 mM ammonium acetate in 70-75% methanol/15-25% acetonitrile/5-10% isopropyl alcohol.

Embodiment 5: Effect of Sample to Internal Standard Volume Ratio on the Test Results In this embodiment, internal standard solutions containing the isotope-labeled fat-soluble vitamins are prepared according to the method described in embodiment 1. The internal standards are dissolved in 75% methanol/15% acetonitrile/10% isopropyl alcohol with 50 mM ammonium acetate. Internal standard solution is mixed with serum samples in different volume ratios (Table 10). Sample preparation and analysis are performed according to the method described in embodiment 1. The peak areas of the six fat-soluble vitamins in the lowest concentration of the standard curve (S1) are listed in Table 10.

TABLE 10

Peak areas of vitamins in different sample to internal standard solution ratios (v/v)

| Sample to internal standard solution volume ratio | Vitamin A | 25-OH vitamin D2 | 25-OH vitamin De | Vitamin E | Vitamin K1 | Vitamin K2 |
|---|---|---|---|---|---|---|
| 1:1 (50 μL sampe to 50 μL internal standard solution) | 40672.9 | 998.9 | 2011.2 | 39793.2 | 2181.0 | 4013.7 |
| 1:3 (50 μL sampe to 150 μL internal standard solution) | 51791.6 | 1357.9 | 3364.7 | 52318.7 | 3269.4 | 5973.1 |
| 1:5 (50 μL sampe to 250 μL internal standard solution) | 54672.9 | 1596.3 | 3514.9 | 56793.2 | 3480.9 | 6265.7 |
| 1:7 (50 μL sampe to 350 μL internal standard solution) | 50180.8 | 1413.7 | 3307.2 | 51639.1 | 3098.5 | 5864.7 |

TABLE 10-continued

Peak areas of vitamins in different sample to internal standard solution ratios (v/v)

| Sample to internal standard solution volume ratio | Vitamin A | 25-OH vitamin D2 | 25-OH vitamin De | Vitamin E | Vitamin K1 | Vitamin K2 |
|---|---|---|---|---|---|---|
| 1:9 (50 μL sampe to 450 μL internal standard solution) | 39245.7 | 1049.5 | 2189.8 | 43187.7 | 2034.6 | 4135.4 |

The results in Table 10 indicate that different volume ratios of the internal standard solution to the sample can greatly affect the recovery rate of the six fat-soluble vitamins from samples. When the volume ratio of the internal standard solution to the sample is 1:1, the proteins in the sample cannot be completely denatured and precipitated, so the extraction efficiency of the fat-soluble vitamins is reduced and the test result is affected by strong matrix effect. When the volume ratio of the sample to the internal standard solution is 1:9, sample is over-diluted, which reduces target response and affects detection sensitivity. Therefore, the volume ratio of the sample to the internal standard solution is preferably 1:3 to 1:7, and optimal at 1:5.

Embodiment 6: Comparison of the Stability of Processed Samples in Different Solvent Systems and Sample Plates In this embodiment, the internal standard solutions are prepared according to the method described in embodiment 1. Internal standard solutions of fat-soluble vitamins in different solvent systems are prepared (Table 11). The standard solutions are processed, put in a sample plate, and stored in the sample chamber for 12 hours before sample injection. The detected concentrations of vitamin K1 in the stored samples and in samples which are processed the same but injected immediately are compared. The deviations of the results from stored samples to the results from samples immediately injected are listed in Table 11.

TABLE 11

Stability of prepared samples in different solvent system and sample plate

| Solvent system | Sample plate | Sample 1 | Sample 2 | Sample 3 |
|---|---|---|---|---|
| 75% methanol/25% acetonitrile | regular | −87.2% | −74.9% | −82.4% |
| 75% methanol/25% acetonitrile with 20 mM ammonium acetate | | −46.7% | −47.7% | −67.5% |
| 75% methanol/25% acetonitrile with 50 mM ammonium acetate | | −55.9% | −57.5% | −56.2% |
| 70% methanol/25% acetonitrile/ 5% isopropanol with 50 mM ammonium acetate | | −18.3% | −9.5% | −19.2 |
| 75% methanol/25% acetonitrile with 50 mM ammonium acetate | Low adsorption | −15.4% | −6.3% | 9.1% |
| 70% methanol/25% acetonitrile/ 5% isopropanol with 50 mM ammonium acetate | | 0.8% | 1.7% | −1.6% |

Vitamin K1 is the least polar analyte among the six fat-soluble vitamins and has a strong tendency to be adsorbed. When it is extracted from the serum using the internal standard solution described in the current invention, it will be adsorbed to the surface of the sample plate well, which could affect the sensitivity and accuracy of its detection.

It can be seen from Table 11 that in the same type of 96-well plate, using a solvent of 70% methanol/25% acetonitrile/5% isopropyl alcohol with 50 mM ammonium acetate that has good solubility for vitamin K1 can reduce the risk of vitamin K1 being adsorbed onto the 96-well plate to some extent, and in turn lower the deviation of detected vitamin K1 value from the actual concentration. By comparing different 96-well plates, it was found that using low adsorption 96-well plate to store sample extracts can increase their stabilities significantly and improve the stability of vitamin K1 test results. Therefor it's preferred to choose low-adsorption 96-well plate in the present invention.

It is to be understood that in the absence of any elements or limitations disclosed herein, illustrations and descriptions in the present invention may be implemented. Thus the illustrations and descriptions disclosed herein are only explanatory rather than limitations, and they are not intended to exclude any equivalents of the features or partial features illustrated and described in the disclosure. Various modifications are possible and fall within the scope of the present invention. Therefore, it is to be understood that although the present invention is disclosed through various embodiments and optional features, modifications and variations of the concepts described herein may be adopted by others skilled in the art, so these modifications and variations also fall within the scope of the present invention defined by the appended claims.

Articles, patents, patent applications, all other reference documents and information which are electronically available are included herein for reference, in their entirety to certain extent, the same as an individual publication being specifically referenced. The applicant reserves the right to incorporate any or all materials and information from such articles, patents, patent applications, and other reference documents into the current invention.

The invention claimed is:
1. A test kit used for high performance liquid chromatography coupled with tandem mass spectrometry to detect six fat-soluble vitamins in a serum sample, comprising:
   an internal standard solution, wherein the internal standard solution comprises;
      five stable isotope labeled fat-soluble vitamins;
      an organic solvent for denaturing protein in the serum sample; and
      ammonium acetate, wherein the organic solvent includes methanol, acetonitrile and isopropyl alcohol, and the volume ratio of methanol to acetonitrile to isopropyl alcohol is 75%:15%:10%; and
   a calibration solution, wherein the calibration solution includes vitamin A, 25-hydroxy vitamin D2, 25-hydroxy vitamin D3, vitamin E, vitamin K1 and vitamin K2, and wherein the six fat-soluble vitamins are vita- min A, 25-OH vitamin D2, 25-OH vitamin D3, vitamin E, vitamin K1, and vitamin K2.

2. The test kit according to claim 1, wherein the concentration of the ammonium acetate in the internal standard solution is 50 mM.

3. The test kit according to claim 1, wherein a matrix of the calibration solution is human serum.

4. The test kit according to claim 3, wherein the test kit further comprises three quality control solutions and wherein each of the quality control solutions includes serum matrix sample with three different concentrations of six fat-soluble vitamins.

5. The test kit according to claim 1, wherein the test kit further comprises two types of mobile phase solutions for liquid chromatography: mobile phase solution A and mobile phase solution B; and wherein the mobile phase solution A is 0.1% formic acid in water and the mobile phase solution B is 0.1% formic acid in methanol.

6. The test kit according to claim 1, wherein the five stable isotope labeled fat-soluble vitamins are vitamin A-d6, 25-OH vitamin D3-d6, 25-OH vitamin D2-d6, vitamin K1-d4, and vitamin E-d6.

\* \* \* \* \*